United States Patent
Hecker et al.

[11] Patent Number: 5,957,128
[45] Date of Patent: Sep. 28, 1999

[54] METHOD AND DEVICE FOR DETERMINATION OF THE FUNCTIONAL RESIDUAL CAPACITY (FRC)

[76] Inventors: Karl-Heinz Hecker, Höhenbergstrasse 57, D-83229 Aschau; Rudolf Schinagl, Fasanenstrasse 177, D-82008 Unterhaching; Thomas O.F. Wagner, Ellernstrasse 41, D-30175 Hannover, all of Germany

[21] Appl. No.: 08/842,179

[22] Filed: Apr. 23, 1997

[51] Int. Cl.⁶ .................................................. A61M 16/00
[52] U.S. Cl. ........................ 128/204.22; 128/203.12; 128/204.24; 600/529; 600/532
[58] Field of Search .................. 128/204.22, 204.23, 128/203.12, 204.24; 600/529, 531, 532, 537, 538

[56] References Cited

U.S. PATENT DOCUMENTS

| | | | |
|---|---|---|---|
| 3,910,261 | 10/1975 | Ragsdale et al. | 600/532 |
| 4,221,224 | 9/1980 | Clark . | |
| 4,788,974 | 12/1988 | Phuc | 128/204.21 |
| 4,941,476 | 7/1990 | Fisher . | |
| 4,947,860 | 8/1990 | Fisher . | |
| 5,069,220 | 12/1991 | Casparie et al. | 600/532 |
| 5,197,481 | 3/1993 | Fisher . | |
| 5,239,994 | 8/1993 | Atkins . | |
| 5,429,123 | 7/1995 | Shaffer et al. . | |
| 5,540,233 | 7/1996 | Larsson et al. | 600/538 |
| 5,575,283 | 11/1996 | Sjoestrand | 128/204.18 |

FOREIGN PATENT DOCUMENTS

| | | |
|---|---|---|
| 0 553 789 A1 | 4/1993 | European Pat. Off. . |
| 29 12 391 B2 | 3/1979 | Germany . |
| 80 15 055 | 6/1980 | Germany . |
| 37 06 559 C2 | 2/1987 | Germany . |
| 37 11 454 A1 | 4/1987 | Germany . |
| 42 32 298 A1 | 9/1992 | Germany . |
| 35 33 557 C2 | 11/1995 | Germany . |

*Primary Examiner*—John G. Weiss
*Assistant Examiner*—V. Srivastava
*Attorney, Agent, or Firm*—Frohwitter

[57] ABSTRACT

The invention relates to a method and a device for determination of functional residual capacity (FRC) by introduction of helium or another inert gas mixture. According to the invention, a measurement apparatus measures the density of the gas mixture upon inspiration and upon expiration at the mouthpiece of a tube or at a mask during forced ventilation of a patient over a plurality of respiratory cycles. The FRC is determined from the difference in the gas concentrations.

7 Claims, 1 Drawing Sheet

METHOD AND DEVICE FOR DETERMINATION OF THE FUNCTIONAL RESIDUAL CAPACITY (FRC)

BACKGROUND OF THE INVENTION

The invention relates to a method for determination of functional residual capacity (FRC), by introduction of helium or another inert gas, using an oscillatory or other determination, wherein a gas mixture containing helium or another inert gas is delivered to a patient or subject in an open system via a respirator or another appliance supporting respiration, and the concentration and quantity of this gas mixture and thus the foreign gas or helium concentration is measured by way of a measurement apparatus connected to the tube or to the mask.

To be able to perform ventilation which does not impose a strain on the patient, it is necessary to know the patient's FRC. In this way the ventilation parameters can be adapted to the patient, the effect of which is that, during ventilation, the patient suffers less damage than when operating with too small or too great an FRC. The physiologically abnormal ventilation is thus mitigated, and the period required to wean the patient off the ventilator is substantially shortened.

It is already known to perform FRC determination by means of oscillatory density measurement, although in the previously known methods this can only be done in a closed system and, consequently, not during mechanical ventilation.

From DE 29 12 391 B2 it is known to carry out analysis of pulmonary function using an appliance with a respiratory bag, where the subject is connected up to the respiratory bag and, by breathing out and rebreathing a test gas mixture containing helium, the change in the density of the gas mixture in the respiratory bag is measured, and from this the FRC is calculated. This involves a closed system in which the subject breathes out into a closed bag and then breathes in again from this bag. For the determination of the FRC, the subject is connected up to the respiratory bag and, after a relatively short period of rebreathing, is again withdrawn from this system. FRC determination during mechanical ventilation is not possible with the known system. U.S. Pat. No. 4,221,224 describes how, in a method for determining the alveolar ventilation, the inspiratory part and the expiratory part of the system are separate from one another. Using the method disclosed, it is not the FRC which is determined, but gas values in the blood.

SUMMARY OF THE INVENTION

The invention is based on the object of making available a method for FRC determination which can also be carried out during mechanical ventilation.

This object is achieved by a method for determination of functional residual capacity (FRC) and other lung volumes by introduction of helium or another inert gas, using an oscillatory or other determination, wherein a gas mixture containing helium or another inert gas is delivered to a patient or subject in an open system via a respirator or another appliance supporting respiration, and the concentration and quantity of this gas mixture and thus the foreign gas or helium concentration is measured by way of a measurement apparatus connected to the tube or to the mask, wherein the concentration or density of the gas mixture, and the volume to be measured in the patients lungs is determined by comparing the measured values of the gas mixtures on inhalation and exhalation, wherein these steps are repeated until the difference between respiratory and expiratory gas concentration in one respiratory cycle falls below a preselected threshold value, or until the future course of the changes in the gas concentration can be predicted from the course in the gas concentrations.

According to a further aspect of the invention, there is provided a device for determination of functional residual capacity (FRC) and other lung volumes by introduction of helium or another inert gas, using an oscillatory or other determination, wherein a gas mixture containing helium or another inert gas is delivered to a patient or subject in an open system via a respirator or another appliance supporting respiration, and the concentration and quantity of this gas mixture and thus the foreign gas or helium concentration is measured by way of a measurement apparatus connected to the tube or to the mask, wherein the concentration or density of the gas mixture, and the volume to be measured in the patients lungs is determined by comparing the measured values of the gas mixtures on inhalation and exhalation, wherein an auxiliary appliance can be connected, via a measurement apparatus, to the mouthpiece of a tube or to a mask via which the ventilated patient or subject is connected to a respirator, in which auxiliary appliance the densities of the gas mixture determine by the measurement apparatus on inhalation and exhalation are evaluated in a CPU.

By virtue of the fact that the FRC determination is achieved in an open system, the method can be carried out during mechanical ventilation, indeed without affecting the latter, and without the preselected respirator parameters having to be changed. An open system is to be understood here as meaning that the exhaled air gets out into the surrounding environment and a new gas mixture is supplied to the subject at each breath. For determination of FRC, the defined addition of helium is started at the end of a respiratory cycle. The helium concentration is determined with regard to inspiration and expiration on each respiratory cycle. The difference in helium is recorded and integrated over a number of respiratory cycles until the difference falls below a preselected threshold value. The size of the FRC is determined from the sum of the quantities of helium remaining in the patient's lungs. Another inert gas can also be used in place of helium. The residual gas quantity contains at least 21% oxygen.

BRIEF DESCRIPTION OF THE DRAWINGS

The invention is explained in greater detail hereinafter on the basis of an illustrative embodiment which is shown in the drawing. The single FIGURE in the drawing is a diagrammatic representation of a device for measuring the FRC in a ventilated patient.

DETAILED DESCRIPTION OF THE INVENTION

Figure 1:
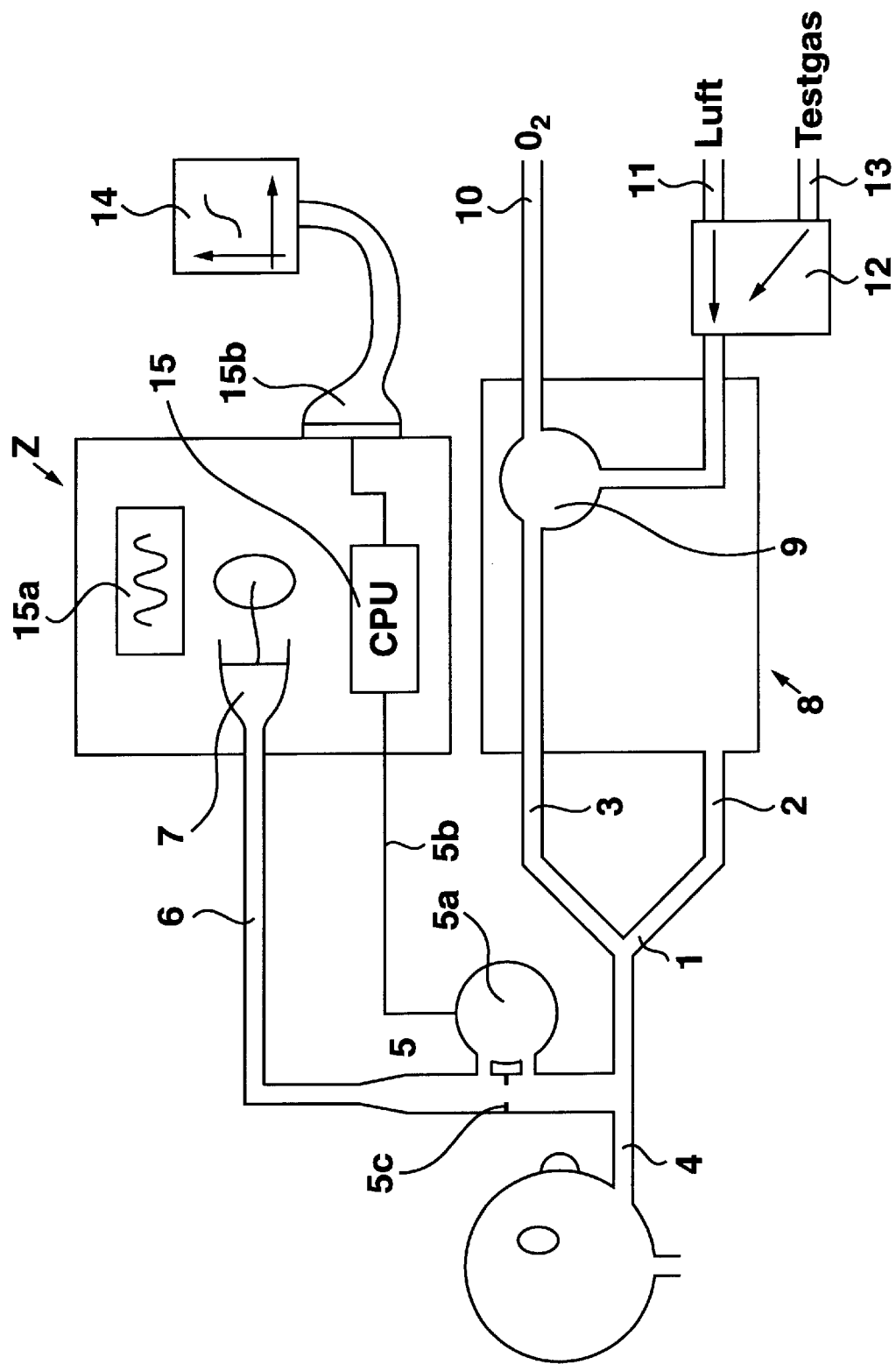

A patient is being ventilated with the aid of a respirator 8. For ventilation, oxygen is fed to the respirator 8 via the connection 10, and air via the connection 11. By means of a valve 12, it is possible to switch from air to test gas on the connection 11, which test gas is supplied via a connection 13.

The ventilation gas which is mixed homogeneously in the respirator 8 by means of a mixing valve 9 is supplied to the mouthpiece 4 of the tube via the inspiration line 3 and the Y-piece 1. During exhalation, the current of exhaled air flows back through the Y-piece 1 and the expiration line 2 into the respirator 8.

An oscillating pump 7 pumps a small amount of air through a pressure line 6 and into a measurement apparatus 5 with a narrowing 5c and a pressure sensor 5a, and the oscillating pressure fluctuations are measured there. The measured value is fed via the data line 5b to the CPU 15 and is evaluated there. The result is indicated on a display 15a. A recorder 14 or a central computer can be connected via corresponding interfaces 15b.

Helium has a substantially lower density than the gases present in the air. This has the effect that when helium is mixed with air, the density of the gas mixture is a linear function of the helium concentration. At the same time, the change in density results in a higher or lower viscosity of the gas mixture, depending on how much helium has been mixed with the air.

If the gas mixture is forced by the pump 7 at a uniform flow rate through the narrowing (aperture) 5c, then a pressure difference is set via the narrowing 5c as a function of the viscosity of the gas. This pressure difference is measured by a pressure sensor 5a and is fed to the CPU 15 via the data line 5b. The addition of helium is begun at the end of the expiration. With the respirator 8, the patient is ventilated with ventilation gas containing a defined concentration of helium. This helium concentration is measured. In the lungs, the helium will also extend to the part of the lungs not emptied on expiration, the FRC. On exhalation, therefore, the exhaled gas has a different, lower concentration of helium. This is once again measured with the measurement apparatus 5, and the result is fed to the CPU 15 via the data line 5b.

The difference in the helium concentration is placed in a memory of the CPU 15 and totaled.

After approximately ten respiratory cycles, the helium concentration is equal on inspiration and expiration. From the sum of the differences in the helium concentration, the CPU 15 calculates the absolute quantity of helium which was introduced into the unemptied region of the lungs. From this absolute quantity of helium, and from the helium concentration of the ventilation gas, the CPU 15 calculates the functional residual capacity FRC.

We claim:

1. A method for determination of the functional residual capacity (FRC) of lungs and lung volume by introduction of helium or another inert gas, using an oscillatory determination means, wherein a gas mixture containing helium or another inert gas is delivered to a patient or a subject in an open system via a respirator or an appliance supporting respiration, and measuring the concentration and quantity of this gas mixture containing helium or another inert gas by a measurement apparatus connected to a tube or to a mask, wherein the concentration or the density of the gas mixture in the lung volume, is determined by comparing the red values of the gas mixtures on inhalation and exhalation, wherein these steps are repeated until the difference between inhalation and exhalation gas concentration in one respiratory cycle falls below a preselected threshold value, or until the future changes in the gas concentrations can be predicted from the measurement of the gas concentrations in the inhalation and exhalation gas concentrations, wherein measuring the concentration is by an oscillatory pressure sensor, and the values measured by the pressure sensor are collected and processed in an algorithm.

2. The method as claimed in claim 1, wherein a mixing valve arranged in the respirator is supplied with 100% oxygen via one supply line and either with a test gas containing a relatively high proportion of helium, or, alternately, with atmospheric air via a second supply line.

3. The method as claimed in claim 1, wherein the result of the FRC measurement is made visible.

4. The method as claimed in one of claims 1 or 3, wherein a pump oscillating at a rate of approximately 10 Hz is connected to the measurement apparatus.

5. A device for determination of the functional residual capacity (FRC) of lungs and lung volume by introduction of helium or another inert gas, using an oscillatory determination means, wherein a gas mixture containing helium or another inert gas is delivered to a patient or a subject in an open system via a respirator or an appliance supporting respiration, and measuring the concentration and the quantity of the gas mixture containing helium or another inert gas by a measurement apparatus connected to a tube or to a mask, wherein the concentration and density of the gas mixture in the lung volume is determined by comparing the measured values of the gas mixtures on inhalation and on exhalation, wherein a CPU control device (15) is connected to a pressure sensor (5a) which is connected to the mouthpiece (4) tube or to a mask through which a patient or a subject is ventilated by a respirator (8) in which the CPU control device (15) determines the densities of the gas mixture on inhalation and on exhalation which are evaluated through the pressure sensor (5a) having an oscillating pump (7).

6. The device as claimed in claim 5 wherein the measurement apparatus (5) has a pressure sensor (5a) which is equipped with a narrowing (5c) and from which the measured values are supplied to the CPU control device (15) via a data line (5b).

7. The device as claimed in claim 5 or 6 wherein a recorder (14) or a central computer is connected to the CPU control device (15) via interfaces (15b).

* * * * *